(12) United States Patent
Viertiö-Oja et al.

(10) Patent No.: US 8,985,107 B2
(45) Date of Patent: Mar. 24, 2015

(54) METHOD, ARRANGEMENT AND COMPUTER PROGRAM PRODUCT FOR RESPIRATORY GAS MONITORING OF VENTILATED PATIENTS

(75) Inventors: Hanna Viertiö-Oja, Espoo (FI); Rene Coffeng, Helsinki (FI)

(73) Assignee: General Electric Company, Schenectady, NY (US)

( * ) Notice: Subject to any disclaimer, the term of this patent is extended or adjusted under 35 U.S.C. 154(b) by 566 days.

(21) Appl. No.: 13/406,621

(22) Filed: Feb. 28, 2012

(65) Prior Publication Data

US 2013/0220323 A1 Aug. 29, 2013

(51) Int. Cl.
*F16K 31/02* (2006.01)

(52) U.S. Cl.
USPC ..................................... 128/204.23; 600/532

(58) Field of Classification Search
USPC ......... 128/204.23, 204.22; 600/529, 531, 532
See application file for complete search history.

(56) References Cited

U.S. PATENT DOCUMENTS

| 3,396,723 | A | 8/1968 | Freytag | |
|---|---|---|---|---|
| 2008/0009762 | A1* | 1/2008 | Hampton et al. | 600/532 |
| 2009/0118633 | A1* | 5/2009 | Jaffe et al. | 600/532 |
| 2011/0126833 | A1 | 6/2011 | Borrello | |

FOREIGN PATENT DOCUMENTS

EP 0521515 A1 1/1993

OTHER PUBLICATIONS

Kugelman et al., "A Novel Method of Distal End-Tidal CO2 Capnography in Intubated Infants: Comparison With Arterial CO2 and With Proximal Mainstream End-Tidal CO2", Pediatrics, vol. 122, No. 6, Dec. 2008, p. 1219-1224.

Klein et al., "Respiratory Gas Monitoring During High-Frequency Jet Ventilation for Tracheal Resection Using a Double-Lumen Jet Catheter", 1998 by the Int'l. Anesthesia Research Society, Anesth Analg 1999; 88:224-226.

Verschuren et al., "Volumetric Capnography as a Screening Test for Pulmonary Embolism in the Emergency Department", Chest, Mar. 2004, 125/3; p. 841-850.

Search Report and Written Opinion from EP Application No. 13156446.0 dated May 14, 2013.

\* cited by examiner

*Primary Examiner* — Steven Douglas
*Assistant Examiner* — Kathrynn Reilly
(74) *Attorney, Agent, or Firm* — Andrus Intellectual Property Law, LLP

(57) ABSTRACT

A method, device, and computer program product for improving accuracy of a respiratory gas measurement from a subject ventilated at a predetermined respiration rate through a ventilator. A respiratory gas measurement value is acquired within a first expiration period of the subject, thereby to obtain a first measurement value. The ventilator is paused for a pause period within a second expiration period of the subject and a respiratory gas measurement is performed within the pause period, thereby to obtain a second measurement value. A correction factor is then determined based on the first measurement value and the second measurement value and the correction factor is employed to correct subsequent respiratory gas measurement values obtained from the subject at the predetermined respiration rate, thereby to improve the accuracy of the measurement.

16 Claims, 3 Drawing Sheets

METHOD, ARRANGEMENT AND COMPUTER PROGRAM PRODUCT FOR RESPIRATORY GAS MONITORING OF VENTILATED PATIENTS

BACKGROUND OF THE INVENTION

This disclosure relates generally to patient monitoring. More particularly, the present invention relates to monitoring of respiratory gas levels of mechanically ventilated patients/subjects. The respiratory gas monitored is typically carbon dioxide.

Carbon dioxide ($CO_2$), which is a byproduct of cell metabolism, is diffused out of the cells to the vascular system and carried by venous circulation to the lungs where it is diffused across the alveolar capillary membrane and exhaled out of the body. Capnometry refers to the (non-invasive) measurement and display of concentration of carbon dioxide in respiratory gases, while a capnometer refers to a machine that produces the $CO_2$ waveforms of respiratory gases. Capnometers measure the concentration of $CO_2$ exhaled at the end of the breath, commonly known as end-tidal breath $CO_2$ ($ETCO_2$). $ETCO_2$ is expressed as a percentage or partial pressure of $CO_2$ in the respiratory gases. Normal values are between 5% and 6%, which is equivalent to 35-45 mmHg. FIG. 1 illustrates a regular time capnogram, i.e. ETCO2 waveform, of a normally breathing subject. A time capnogram comprises two basic segments, an inspiratory segment and an expiratory segment. During the first portion of expiration (time period 1), $CO_2$ level remains zero as the initial gas sampled by the sensor will be from a so-called dead space. As the expiration continues, $CO_2$ level rises to the above-mentioned normal level as the $CO_2$ rich gases from the alveoli reach the sensor (time period 2). At the end of the expiration (time period 3), $CO_2$ level drops to zero as the subject starts to inspire $CO_2$ free gases.

At present, a capnometer is a standard tool for monitoring $CO_2$ levels of subjects in anesthesia and intensive care, for example. This is because $CO_2$ levels and waveforms provide rapid and reliable information that helps to detect and prevent various life threatening events, such as malposition of tracheal tubes and failures in metabolic, cardiovascular and respiratory systems.

Total ventilation may be divided between two parts: the respiratory gases that exchange with pulmonary blood and the respiratory gases that do not exchange with the pulmonary blood. The former is commonly called pulmonary ventilation, while the latter is commonly called dead space ventilation. Dead space thus refers to the respiratory gases that are inhaled but which do not take part in the gas exchange. Physiological dead space may be divided into anatomical dead space and alveolar dead space. Anatomical dead space comprises the gases in the upper airways, such as mouth and trachea, which do not come into contact with the alveoli of the lungs. Alveolar dead space comprises the gases that come into contact with the alveoli without any gas exchange, i.e. without any perfusion taking place. A third form of dead space is commonly termed mechanical or equipment dead space. This is formed by the gases that fill the breathing circuits of a mechanical ventilator system without participating in the gas exchange.

Dead space tends to decrease the $ETCO_2$ readings since the "dead" gas/air that does not participate in gas exchange mixes with the expired gases and thus dilutes the expired $CO_2$. In other words, all the dead space gas in anatomical and equipment dead spaces is not normally exhaled in the beginning of the expiration period but part of the dead space gas mixes with the exhaled $CO_2$ rich gases and dilutes the expired $CO_2$. This may in turn deteriorate the reliability of the correlation with the blood gas $CO_2$ concentrations and lead to underestimation of the arterial $CO_2$ level. Generally, the smaller the patient the greater the effect of dead space. In small patients, the accuracy of capnometry has been increased by using small-volume endotracheal tube connectors and/or using special endotracheal tubes that allow $CO_2$ samples to be taken from the tip of the tube (instead of a regular mouth sensor).

A further factor that may affect the accuracy of the $ETCO_2$ measurement and thus also the reliability of the correlation between $ETCO_2$ and blood $CO_2$ is the respiration rate. As the respiration rate increases, the inspiration and expiration periods shorten and the expiration period may become too short for transferring all $CO_2$ rich gases to the sensor before the next inspiration period starts. This in turn leads to rebreathing, i.e. exhaled gas mixes with the gas in the ventilation system and some of the mixed gas is reinhaled.

Consequently, the accuracy and reliability of the $ETCO_2$ measurement and blood $CO_2$ estimation may become compromised in certain ventilation conditions. As discussed above, the risk of inaccurate $ETCO_2$ measurement is greater when infants and high frequency ventilation are involved. However, high frequency ventilation, which is typically employed to reduce lung injuries or to prevent further lung injuries, may be applied to patients of all ages, from neonates to adults.

BRIEF DESCRIPTION OF THE INVENTION

The above-mentioned problems are addressed herein which will be comprehended from the following specification. In the disclosed solution, the ventilator is paused during an expiration period and the measurement is performed at the end of the pause before normal high frequency respiration rhythm is restored. In other words, one of the expiration periods is made longer, thereby to obtain a measurement value corresponding to a longer expiration of the subject. A correction factor is determined based on the measurement value obtained from the longer expiration and a measurement value obtained from a regular (shorter) expiration. Subsequent measurement values may then be corrected through the correction factor. The correction factor is specific to the respiration rate and a new correction factor may be determined for a new respiration rate.

In an embodiment, a method for improving the accuracy of a respiratory gas measurement from a ventilated subject comprises ventilating the subject at a predetermined respiration rate through a ventilator, acquiring a respiratory gas measurement value within a first expiration period of the subject, thereby to obtain a first measurement value, and pausing the ventilator for a pause period within a second expiration period of the subject. The method further includes performing a respiratory gas measurement within the pause period, thereby to obtain a second measurement value, determining a correction factor based on the first measurement value and the second measurement value, and using the correction factor to correct subsequent respiratory gas measurement values obtained from the subject at the predetermined respiration rate.

In another embodiment, an arrangement for improving the accuracy of a respiratory gas measurement from a ventilated subject comprises a ventilator unit adapted to ventilate a subject at a predetermined respiration rate, a measurement unit adapted to acquire a respiratory gas measurement value within a first expiration period of the subject, thereby to obtain a first measurement value, and a ventilator control unit adapted to pause the ventilator unit for a pause period within a second expiration period of the subject, wherein the measurement unit is further adapted to perform a respiratory gas measurement within the pause period, thereby to obtain a second measurement value. The arrangement further includes a ventilator processing unit adapted to determine a correction factor based on the first measurement value and the second measurement value and to use the correction factor to correct subsequent respiratory gas measurement values obtained from the subject at the predetermined respiration rate.

In a still further embodiment, a computer program product for improving accuracy of a respiratory gas measurement of a ventilated subject comprises a first program product portion adapted to pause a ventilator for a pause period during an expiration period of the subject and a second program product portion adapted to determine a correction factor based on a first respiratory gas measurement value and a second respiratory gas measurement value, wherein the first respiratory gas measurement value is obtained at end of a regular expiration cycle of the subject and the second respiratory gas measurement value is obtained within the pause period. The computer program product further includes a third program product portion adapted to use the correction factor to correct subsequent respiratory gas measurement values obtained from the subject at current respiration rate.

Various other features, objects, and advantages of the invention will be made apparent to those skilled in the art from the following detailed description and accompanying drawings.

DETAILED DESCRIPTION OF THE INVENTION

Figure 2:
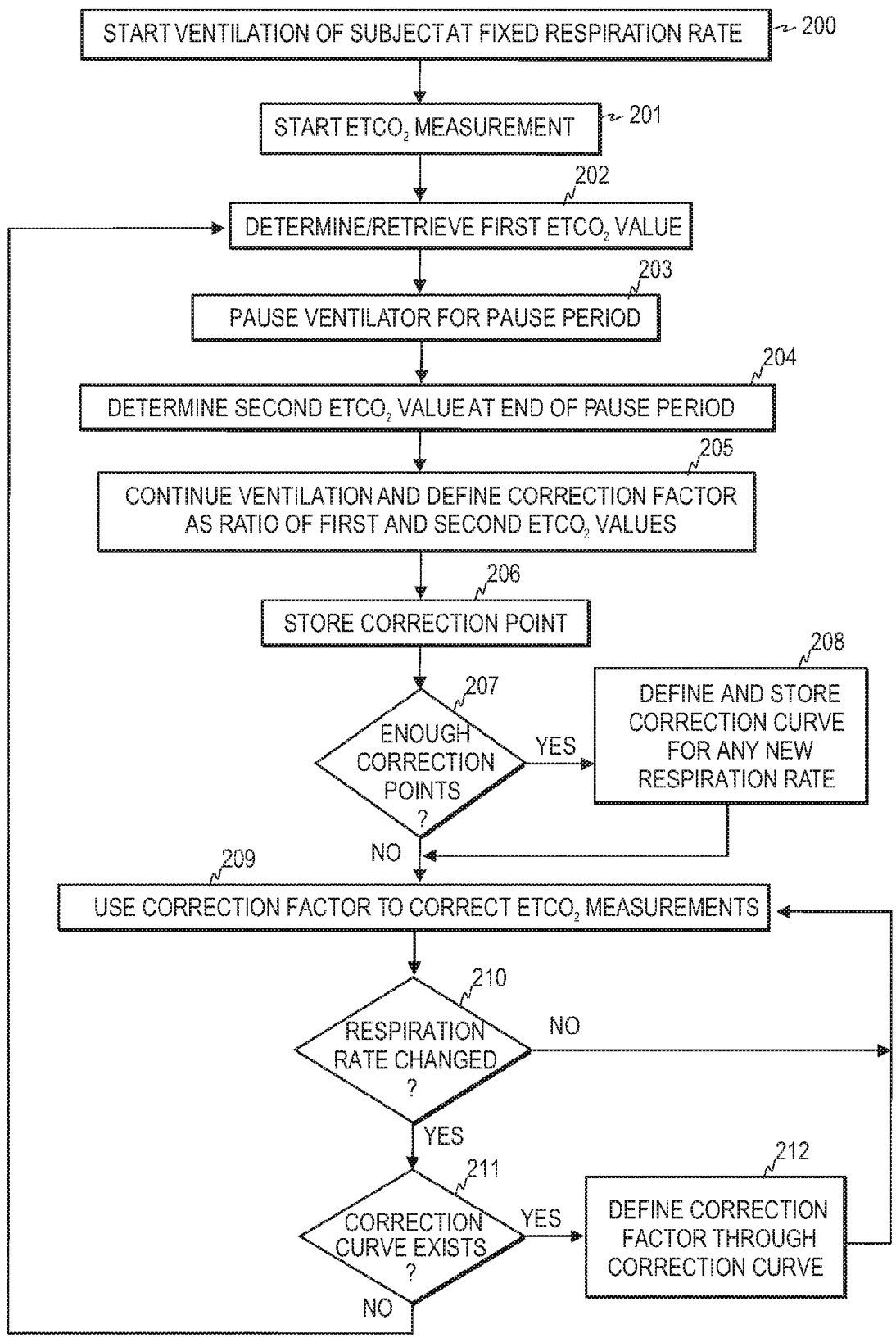
FIG. 2 is a flow diagram illustrating one embodiment of a method for improving the accuracy of a respiratory gas measurement of a ventilated subject.

FIG. 2 illustrates one embodiment of a method for improving the accuracy of a respiratory gas measurement of a ventilated subject. It is assumed here that the patient/subject is ventilated at a substantially fixed respiration rate (step 200) and that $ETCO_2$ measurements are made (step 201) from the patient/subject. An $ETCO_2$ value may be measured, for example, at the end of each expiration of the subject. The ventilation rate is typically rather high, such as 150 breaths per minute, since the mechanism for improving the accuracy of the $ETCO_2$ measurement is intended mainly for high respiration rates, at which the reliability of the measurement is more compromised than at low respiration rates. It is further assumed that the mean airway pressure of the subject remains substantially unchanged at a particular respiration rate, i.e. that the ventilator settings are not changed so that the mean airway pressure would change when the subject breathes at a particular rate.

For continuous and non-invasive $ETCO_2$ monitoring, the $ETCO_2$ measurement is in this example performed at a location proximal to the endotracheal tube. For creating a correction factor for the current respiration rate, a first $ETCO_2$ value is determined or retrieved from the $ETCO_2$ time series (step 202). The ventilator is then paused at the end of an expiration for a predetermined pause period (step 203), thereby to make this expiration cycle longer. A second $ETCO_2$ measurement value is determined substantially at the end of the pause period (step 204). The second sample is thus obtained at the end of an expiration that is longer than the previous expirations, thereby to obtain the second measurement value after a more complete emptying of the lungs.

Figure 1:
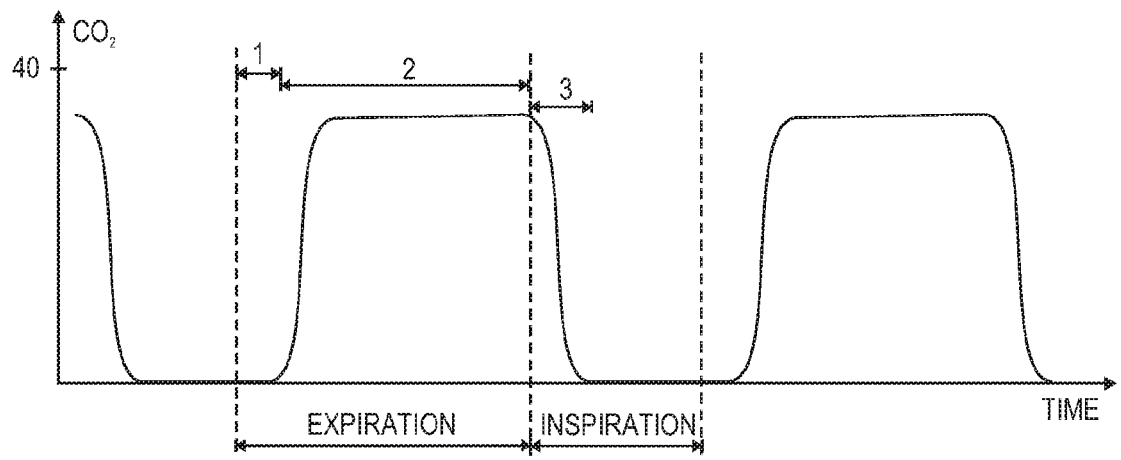
FIG. 1 illustrates an example of a time capnogram of a normally breathing subject.
Figure 3:
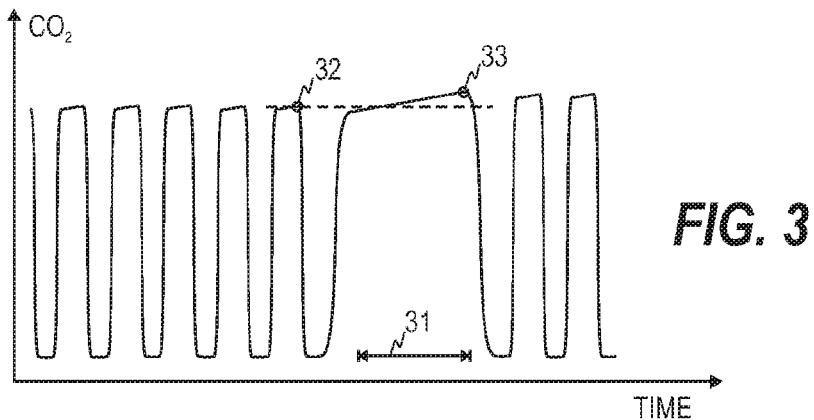
FIG. 3 illustrates an example of the two respiratory gas measurements used to define a correction factor for subsequent respiratory gas measurements.

After the pause period, which typically lasts two to three seconds, the ventilator continues its operation at the fixed respiration rate (step 205). A correction factor CF may be determined (step 205) as the ratio of the second and first measurement values: $CF=(ETCO_2)_k/(ETCO_2)_{k-1}$, where $(ETCO_2)_k$ is the second measurement value obtained at the end of the pause and $(ETCO_2)_{k-1}$ is the first measurement value obtained from a regular (shorter) expiration. As indicated by the subscripts, the first and second measurement values may represent temporally consecutive $ETCO_2$ measurements that may be obtained from successive expirations. FIG. 3 shows a time capnogram that illustrates an example of the pause period 31 and the first and second measurements 32 and 33, respectively.

The ratio and the respective respiration rate form a data point on a coordinate system (shown below in FIG. 4) where one axis, such as the X axis, represents respiration rate and where the other axis, such as the Y axis, represents the correction factor. This data point is termed correction point in this context. With reference to FIG. 2 again, the correction point is stored at step 206.

After the storing of a new correction point, the ventilator system may check at step 207 whether there are enough correction points in the memory for the determination of a correction curve, i.e. a curve that fits to the collected data points. However, after the first correction point this is not the case, since at least three correction points are needed to produce a fitting curve. The ventilator system then uses the correction factor to correct the subsequent $ETCO_2$ measurement values: $ETCO_2=(ETCO_2)_m \times CF$, where $ETCO_2$ is the corrected value, $(ETCO_2)_m$ the measured value, and where the correction factor CF is the above ratio that depends on the respiration rate (step 209).

The same correction factor may used in step 209 as long as the respiration rate remains the same. However, if the respiration rate changes (step 210/yes), the ventilator system may repeat steps 202 to 207 and 209, thereby to define a new correction point for the new respiration rate. These steps may be repeated until enough correction points have been determined and stored for the determination of the correction curve. When the number of correction points reaches this limit, the ventilation system detects at step 207 that the correction curve may be determined and jumps to step 208 in which the stored correction points may be used for producing a curve that has the best possible fit to the points. This may be carried out through order regression, for example. When the correction curve has been generated, the ventilation system may use the curve to define the correction factor for any new respiration rate (step 212) without having to pause the ventilator.

Figure 4:
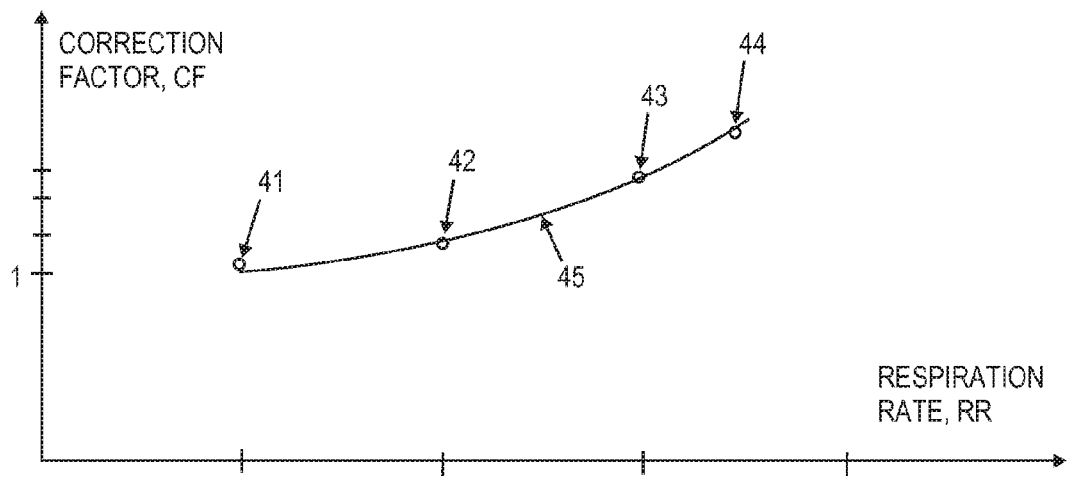
FIG. 4 illustrates an example of correction factors and the respective correction curve determined for a respiratory gas measurement.

FIG. 4 illustrates four different correction points 41 to 44 determined in steps 202 to 206 respectively for four different respiration rates. FIG. 4 also illustrates a correction curve 45 defined based on the correction points. At low respiration rates, the correction factor is close to one and increases as the respiration rate increases making the expiration periods shorter. After a predetermined number of correction points have been obtained, the control and processing may use $n^{th}$ order regression, for example, to search for a curve $CF(RR) = C + C_1 \times RR + C_2 \times (RR)^2 + \ldots + C_n \times (RR)^n$ that provides the best fitting to the correction points (where RR represents the respiration rate). The curve, i.e. the coefficients $C_i$ ($i=1, 2, \ldots, n$) and the constant C, is stored as the correction curve, cf. step 208.

In the above embodiments, the correction factor is determined as the ratio of the second measurement value to the first measurement value. As is obvious here, the correction factor may also be determined as the ratio of the first measurement value to the second measurement value, in which case corrected $ETCO_2$ values are obtained by dividing the measured values by the correction factor CF: $ETCO_2 = (ETCO_2)_m / CF$.

It is assumed above that the mean airway pressure remains substantially constant at a particular respiration rate. If the mean airway pressure changes, a recalibration, i.e. a new determination of the correction point(s)/curve is to be initiated. The mean airway pressure may be changed by changing the tidal volume, the peak airway pressure or the positive end-expiratory pressure (PEEP). A change in the PEEP may be caused by a change in the extrinsic PEEP supplied by the ventilator or the intrinsic PEEP (which depends on the respiration rate).

In a further embodiment, the inspired $CO_2$ value may be measured and deducted from the measured $CO_2$ values when determining the correction factor: $CF = [(ETCO_2)_k - FiCO_2] / [(ETCO_2)_{k-1} - FiCO_2]$, where $FiCO_2$ is the inspired $CO_2$ measured during a (short) inspiration period. This embodiment is mainly for high respiration rates, since the inspired $CO_2$ level is normally zero at lower respiration rates. However, rebreathing may start to occur as the respiration rate increases, which also results in inhaled $CO_2$.

The above examples relate to $CO_2$ measurement, which is a common measurement in anesthesia and in intensive care, for example. However, the above-described mechanisms may also be employed to improve the accuracy of the concentration measurement of another respiratory gas than carbon dioxide. Such a respiratory gas may be, for example, oxygen or any volatile anesthetic agent, such as isoflurane or sevoflurane. In the measurement of a non-$CO_2$ respiratory gas, the above form $CF = [(ETXX)_k - FiXX] / [(ETXX)_{k-1} - FiXX]$ (or the inverse thereof) may be used as the correction factor, since the inspired concentration FiXX is not zero. Here $(ETXX)_k$ refers to the concentration of the non-$CO_2$ respiratory gas at the end of the pause and $(ETXX)_{k-1}$ to the concentration of the said gas at the end of a regular (shorter) expiration.

Figure 5:
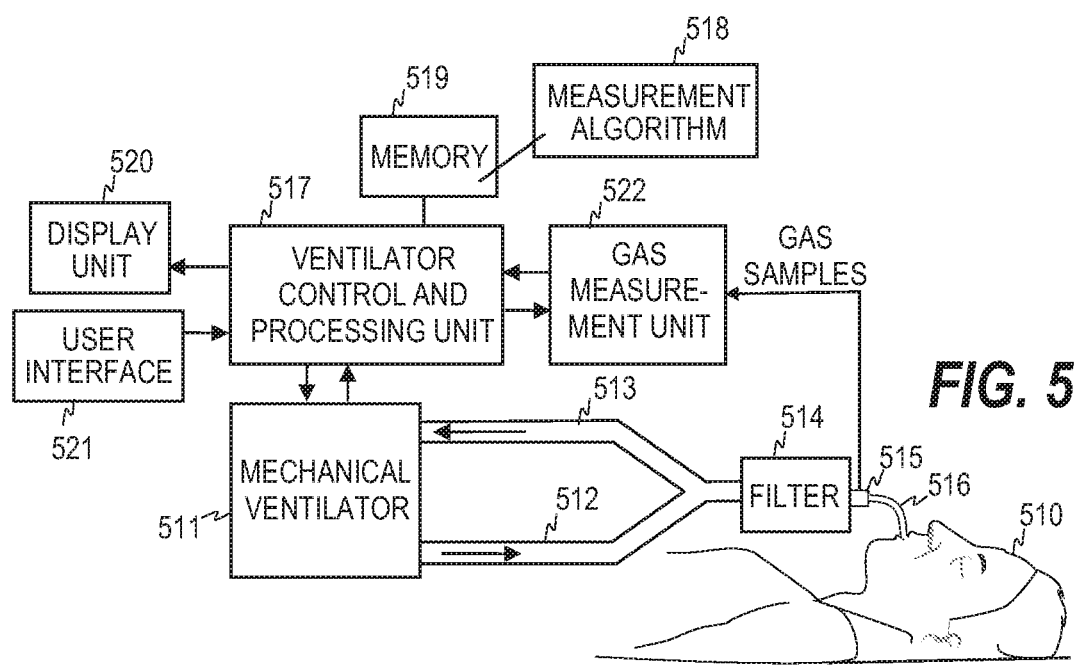
FIG. 5 illustrates an example of a ventilator system including proximal respiratory gas measurement provided with accuracy enhancement.

FIG. 5 schematically illustrates an embodiment of a ventilator system provided with the above proximal respiratory gas measurement, such as $ETCO_2$ measurement. A mechanical ventilator 511 generates a controlled flow of gas in its inhalation system (not shown) and supplies the gas flow through an inhalation tube 512, a (bacterial) gas filter 514, and an endotracheal tube 516 into the airways of a subject/patient 510. A control and processing unit 517 is configured to adapt the pressure and flow characteristics to the needs of the subject, which may be defined by the user through a user interface 521 of the ventilator system.

The expiratory gas returns from the lungs of the subject through the endotracheal tube, the gas filter and an exhalation tube 513 to the exhalation circuit (not shown) of the ventilator. It assumed here that the gas sensor 515, which is typically a $CO_2$ sensor, is a sidestream sensor located on the endotracheal tube or between the endotracheal tube and the gas filter.

The gas samples are supplied to a gas measurement unit 522 configured to measure the gas concentration values based on the gas samples. The gas measurement unit is operably connected to the control and processing unit 517 which is provided with a gas measurement algorithm 518 that includes the above accuracy enhancement functionality. The measurement algorithm, which may be stored in a memory 519 of the control and processing unit, may be configured to perform the steps of FIG. 2, for example, when executed by the control and processing unit.

The control and processing unit is further adapted to control a display unit 520 to display the measured waveforms, such as time capnograms, measurement results and other user information, such as ventilator settings, on the screen of the display unit. In terms of the respiratory gas measurement, the control and processing unit may be divided into two parts: a control unit configured to control the operation of the ventilator system and a processing part configured to produce the corrected gas concentration values based on measured gas concentration values.

A conventional ventilator system may also be upgraded to enable respiratory gas measurements according to the above mechanism. Such an upgrade may be implemented, for example, by delivering to the control and processing unit a software unit that includes the entire software system or desired parts thereof. Consequently, the software unit comprises at least a first portion adapted to pause the ventilator for a pause period during an expiration period of the subject, a second program product portion adapted to determine a correction factor based on the first and second gas measurement values, and a third program product portion adapted to use the correction factor to correct subsequent gas measurement values obtained from the subject at current respiration rate. The software unit may also comprise a fourth portion configured to determine the correction curve. The first and second gas measurement values may be obtained from an existing measurement unit, such as a capnometer.

In the above embodiments, the correction curve is determined after a predetermined number of correction points have been obtained. The correction points may be determined during a separate training period preceding the actual monitoring or during the monitoring of the subject as new correction points are needed. If it is known that the respiration rate will remain substantially constant, there is no need to determine the correction curve, but the correction factor may be determined at regular intervals, such as every 2 minutes, to keep the correction factor updated. In one embodiment, the determination of the correction curve may be omitted and the correction factor may be determined through pausing of the ventilator each time the respiration rate is changed.

Since the benefits of the disclosed gas measurement correction are more prominent at high respiration rates, the above mechanism is more useful at high-frequency ventilation than in conventional ventilation. However, the mechanism may be employed in any ventilator and ventilating mode where it is possible to produce a longer breath intermittently, thereby to obtain the correction factor. Moreover, although the above mechanism is more useful in connection with neonates and infants due to the emphasized effect of dead space in small patients, it may be used for patients of all ages.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural or operational elements that do not differ from the literal language of the claims, or if they have structural or operational elements with insubstantial differences from the literal language of the claims.

The invention claimed is:

1. A method for improving accuracy of a respiratory gas measurement from a ventilated subject, the method comprising:
   ventilating a subject at a predetermined respiration rate through a ventilator;
   acquiring a respiratory gas measurement value within a first expiration period of the subject, thereby to obtain a first measurement value;
   pausing the ventilator for a pause period within a second expiration period of the subject;
   performing a respiratory gas measurement within the pause period, thereby to obtain a second measurement value;
   determining a correction factor based on the first measurement value and the second measurement value; and
   using the correction factor to correct subsequent respiratory gas measurement values obtained from the subject at the predetermined respiration rate.

2. The method according to claim 1, further comprising measuring respiratory gas values during successive expiration periods of the subject, thereby to obtain a time series of respiratory gas values, wherein the acquiring includes selecting a respiratory gas value from the time series.

3. The method according to claim 2, wherein the selecting, includes selecting the latest respiratory gas value from the time series, and wherein the pausing is initiated in response to the selecting.

4. The method according to claim 1, wherein the determining includes determining the correction factor, in which the correction factor represents a ratio of the first and second measurement values.

5. The method according to chum 1, further comprising repeating the acquiring, pausing, performing, determining and using when a predetermined event occurs, in which the predetermined event is one of a change in respiration rate of the subject and a change in mean airway pressure of the subject.

6. The method according to claim 5, further comprising defining a correction curve based on a plurality of data points, wherein each data point comprises a correction factor and respective respiration rate and wherein the correction curve indicates a correction factor for any new respiration rate.

7. The method according to claim 5, wherein the defining comprises using $n^{th}$ order regression to produce a fitting curve that fits to the plurality of data points, wherein the fitting curve represents the correction curve.

8. The method according to claim 1, wherein the acquiring includes acquiring the first measurement value and the performing includes obtaining the second measurement value, in which the first measurement value and the second measurement value represent carbon dioxide concentrations.

9. An arrangement for improving accuracy of a respiratory gas measurement from a ventilated subject, the arrangement comprising:
   a ventilator unit adapted to ventilate a subject at a predetermined respiration rate;
   a measurement unit adapted to acquire a respiratory gas measurement value within a first expiration period of the subject, thereby to obtain a first measurement value;
   a ventilator control unit adapted to pause the ventilator unit for a pause period within a second expiration period of the subject;
   wherein the measurement unit is further adapted to perform a respiratory gas measurement within the pause period, thereby to obtain a second measurement value; and
   a ventilator processing unit adapted to determine a correction factor based on the first measurement value and the second measurement value and to use the correction factor to correct subsequent respiratory gas measurement values obtained from the subject at the predetermined respiration rate.

10. The arrangement according to claim 9, wherein the measurement unit is further adapted to
    measure respiratory gas values during successive expiration periods of the subject, thereby to obtain a time series of respiratory gas values; and
    acquire the first measurement value by selecting a respiratory gas value from the time series.

11. The arrangement according to claim 10, wherein the measurement unit is adapted to select the latest respiratory gas value from the time series, and wherein the ventilator control unit is adapted to pause the ventilator unit in response to selection of the latest respiratory gas value.

12. The arrangement according to claim 9, wherein the correction factor represents a ratio of the first and second measurement values.

13. The arrangement according to claim 9, wherein the ventilator control unit is adapted to initiate determination of a new correction factor when a predetermined event occurs, in which the predetermined event is one of a change in respiration rate of the subject and a change in mean airway pressure of the subject.

14. The arrangement according to claim 13, wherein the ventilator processing unit is further adapted to define a correction curve based on a plurality of data points, wherein each data point comprises a correction factor and a respective respiration rate and wherein the correction curve indicates a correction factor for any new respiration rate.

15. The arrangement according to claim 14, wherein the ventilator processing unit is adapted to use $n^{th}$ order regression to produce a fitting curve that fits to the plurality of data points, wherein the fitting curve represents the correction curve.

16. The arrangement according to claim 9, wherein the first and second measurement values represent carbon dioxide concentrations.

* * * * *